United States Patent
Hartman

(10) Patent No.: US 9,351,838 B2
(45) Date of Patent: May 31, 2016

(54) DEFORMABLE PROSTHESIS

(71) Applicant: Biomet Manufacturing, LLC, Warsaw, IN (US)

(72) Inventor: Christopher Hartman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 110 days.

(21) Appl. No.: 14/149,161

(22) Filed: Jan. 7, 2014

(65) Prior Publication Data

US 2015/0190231 A1 Jul. 9, 2015

(51) Int. Cl.
*A61F 2/32* (2006.01)
*A61F 2/34* (2006.01)
*A61F 2/30* (2006.01)

(52) U.S. Cl.
CPC .......... *A61F 2/34* (2013.01); *A61F 2002/30072* (2013.01); *A61F 2002/30369* (2013.01); *A61F 2002/30485* (2013.01); *A61F 2002/30583* (2013.01); *A61F 2002/3438* (2013.01)

(58) Field of Classification Search
CPC .................. A61F 2/34; A61F 2002/3438
See application file for complete search history.

(56) References Cited

U.S. PATENT DOCUMENTS

| 5,002,577 A | 3/1991 | Bolesky et al. |
| 5,080,678 A | 1/1992 | Spotorno et al. |
| 5,800,555 A | 9/1998 | Gray, III |
| 6,527,809 B1 | 3/2003 | Doursounian et al. |
| 7,294,150 B1 | 11/2007 | Mandell et al. |
| 7,776,097 B2 | 8/2010 | Tepic et al. |
| 8,070,823 B2 * | 12/2011 | Kellar et al. ................. 623/23.4 |
| 8,840,676 B2 * | 9/2014 | Belew ................... A61F 2/4684 623/22.15 |
| 2013/0079887 A1 | 3/2013 | Grostefon et al. |

OTHER PUBLICATIONS

Par 5™, Protrusio Acetabular Reconstruction System Brochure, Biomet Orthopedics Inc., 12 pages (2006).

* cited by examiner

*Primary Examiner* — Brian Dukert
(74) *Attorney, Agent, or Firm* — Schwegman Lundberg & Woessner, P.A.

(57) ABSTRACT

A deformable prosthetic member, including an acetabular shell, can be formed of appropriate materials to engage a liner. The deformable member can include one or more feature to deform and engage a second member, such as a liner, in a selected position. A plurality of deformable features allows for a plurality of possible positions for the second member.

7 Claims, 7 Drawing Sheets

DEFORMABLE PROSTHESIS

BACKGROUND

This section provides background information related to the present disclosure which is not necessarily prior art.

A prosthetic device can be positioned in an anatomy for various purposes. For example, the anatomy can be damaged or injured such that a prosthetic device can replace a portion of the anatomy. The prosthetic device can be positioned in various portions of the anatomy to replace or augment the natural anatomy.

A prosthetic device can include a portion that can assist in replacing or repairing a portion of a joint. For example, in a human patient or subject, various joints allow bone portions to move and articulate relative to one another. In a hip joint, an acetabulum allows a femoral head to articulate relative to the pelvis. After an injury or disease process, the acetabulum may not properly articulate with a proximal femoral portion. Accordingly, a prosthesis can be used to replace the acetabulum to assist in anatomical or substantially near anatomical motion of the joint.

Generally, the prosthetic members include specific features that are designed to not be altered, substantially, during an implantation or use. For example, a prosthetic cup can be designed to incorporate or attach to a prosthetic liner that includes a high wall or an angle. Examples include the PAR5™ Acetabular Reconstruction System sold by Biomet, Inc., having a place of business in Indiana. The system includes high wall liners, angled liners, neutral faced liners and high-walled angled liners.

SUMMARY

This section provides a general summary of the disclosure, and is not a comprehensive disclosure of its full scope or all of its features.

A prosthesis positioned within a subject, such as a human anatomy, can be deformed to engage a second prosthetic member in one of a selected plurality of orientations or positions. For example, the acetabular shell, as a first prosthetic member, can be positioned within an acetabulum of a patient. A liner, such as a polymer liner, can be positioned within the acetabular shell. The liner can engage the shell and deform a portion of the shell to seat or fix the liner in a selected orientation relative to the shell. The liner can be engaged within the shell and fixed in the shell, due to the deformable nature of the shell, other than axial positioning within the shell. Further, the shell, either alone being deformed with the liner or separately therefrom, can be deformed into the liner to hold the liner in the selected orientation when positioned. Thus, the liner can be positioned within the shell at one of a plurality of positions.

The deformable prosthetic member, including an acetabular shell, can be formed of appropriate materials to engage a liner. It is understood, however, that the liner and the shell can be formed of the same material. Moreover, the first prosthetic member can be other implant members such as a distal femoral component, a proximal tibial component, humeral or glenoid components, or selected members. For example, a proximal tibial tray can be positioned within the tibia and a liner can be selectively engaged with the tibial tray.

Prosthetic members, such as acetabular implants, can be used to replace portions of the anatomy. An acetabulum can be replaced and/or augmented with an acetabular implant using various prosthesis members. A prosthetic member can be positioned within an acetabulum and a prosthetic liner, also referred to as an acetabular liner, can be engaged within a prosthetic member. Generally, a prosthetic acetabulum can include an acetabular shell and an acetabular liner.

An acetabular liner can be engaged within a prosthetic shell in one of a plurality of positions and/or orientations. Generally, the liner is positioned within the shell in a selected configuration and held in place with various fixation techniques. For example, a liner can be positioned within the shell to engage one or more deformable features and/or allow one or more deformable features to engage the liner to hold the liner in a selected position.

The acetabular shell can include an external surface provided and configured to engage an acetabulum of a patient, as discussed further herein. The acetabular shell can include an internal surface that is configured to engage a liner. An internal surface can include a positive feature that is deformable by a liner to assist in fixing the liner in a selected location. Further or alternatively, the shell can include a negative feature that is able to deform to engage the liner after positioning the liner in a selected position. Various deformable features, either positive or negative, can include one or more round protrusions, such as a circular protrusion, or a ring protrusion or negative feature formed by the shell. In various embodiments, the protrusions may also have a non-round shapes. Exemplary protrusion shapes may include polygon, rhombus, or any other suitable shape.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
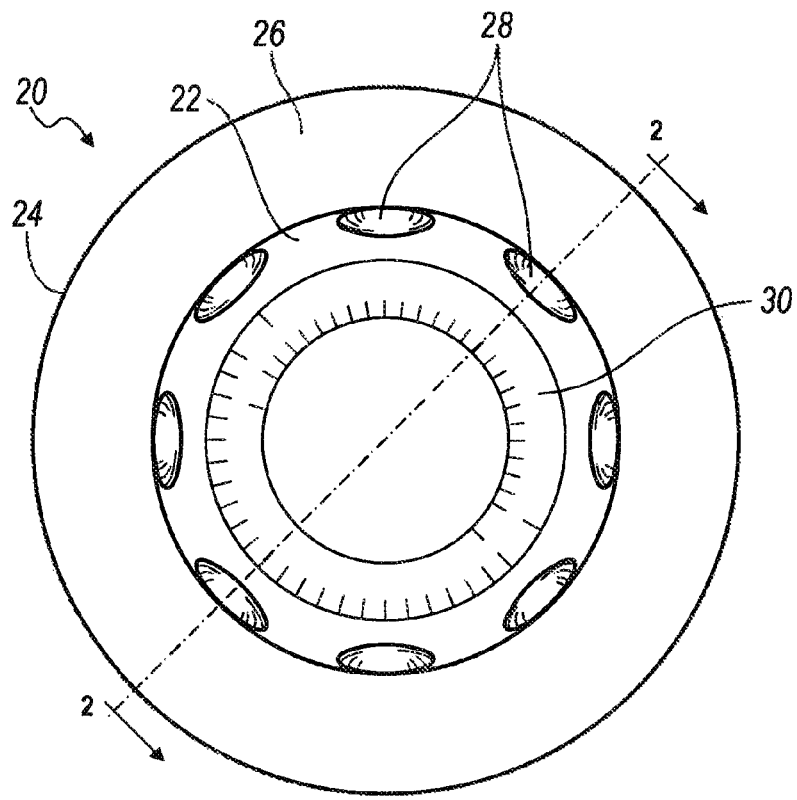
FIG. 1 is a top plan view of a shell, according to various embodiments.

With reference to FIG. 1, an acetabular shell 20, according to various embodiments, is illustrated. The acetabular shell 20 may include an internal surface 22 and an external surface 24 and a top surface 26 extending between the internal surface 22 and the external surface 24. The internal surface 22 can include one or more liner connection features. The liner connection features may include one or more positive connection circles or individual protrusions 28 and one or more continuous protrusions, such as a ring 30. It is understood that more or less than the single protrusions 28 or the continuous protrusion 30 can be provided. Moreover, as illustrated in FIG. 1, the liner engaging features can be spaced throughout the shell 20. For example, the individual protrusion 28 may be near the upper surface 26, such as about 2 millimeters (mm) to about 10 mm from the upper surface, and the annular protrusion 30 may be nearer an apex, such as about 10 mm to about 30 mm, than the individual protrusions 28. It is understood, however, that the locations of the various liner engaging features can be reversed or otherwise varied.

Figure 2:
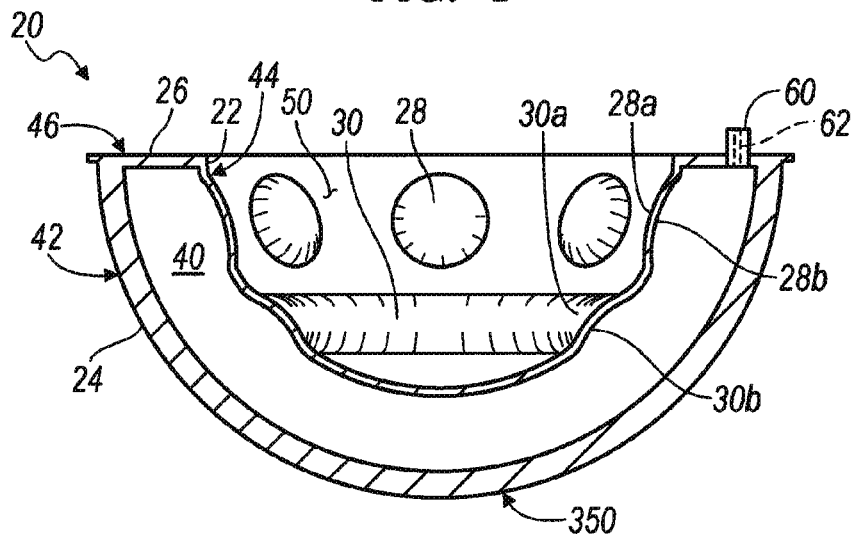
FIG. 2 is a cross-sectional view along line 2-2 of FIG. 1 of the shell.

With continuing reference to FIG. 1, and additional reference to FIG. 2, the acetabular shell 20 is illustrated. As illustrated in FIG. 2, the acetabular shell 20 can include an opening or void 40 between an external wall 42 that has the external surface 24 and an internal wall 44 that has the internal surface 22. Further, an upper or rim wall 46 may have the upper surface 26 and completely enclose the void 40.

The protrusions, such as the individual protrusions 28 and the annular protrusion 30 can be formed as features or shapes of the internal wall 44 and augmentations or changes of the internal surface 22. As illustrated in FIG. 2, the singular protrusion 28 can be formed as a portion of a sphere, such as a hemisphere, that has a curved (such as in a portion of a spherical shape) protruding portion 28a into a central or liner void 50 of the shell 20. The singular protrusion 30 can include a protruding portion 30a that extends, such as from the internal wall, 44 into the central or liner void 50. As further illustrated in FIG. 2, the protruding portions 28a and 30a can form negative regions, such as a negative portion 28b and a negative portion 30b from the internal void area 40 of the shell 20. Accordingly, the wall 44 may be a substantially thin wall that can be formed with the protrusions 28, 30 for engaging a liner, as discussed further herein.

The shell 20 can further include a fill port or fill member 60 that includes an internal passage 62 that allows a material to pass into the internal void 40 for various purposes. The void filling material to fill the internal void 40 may provide a rigid structure between the internal wall 44 and the external wall 42, as discussed further herein. Generally, the void filing material can include a non-compressible material such as saline, bone cement, etc.

Figure 3:
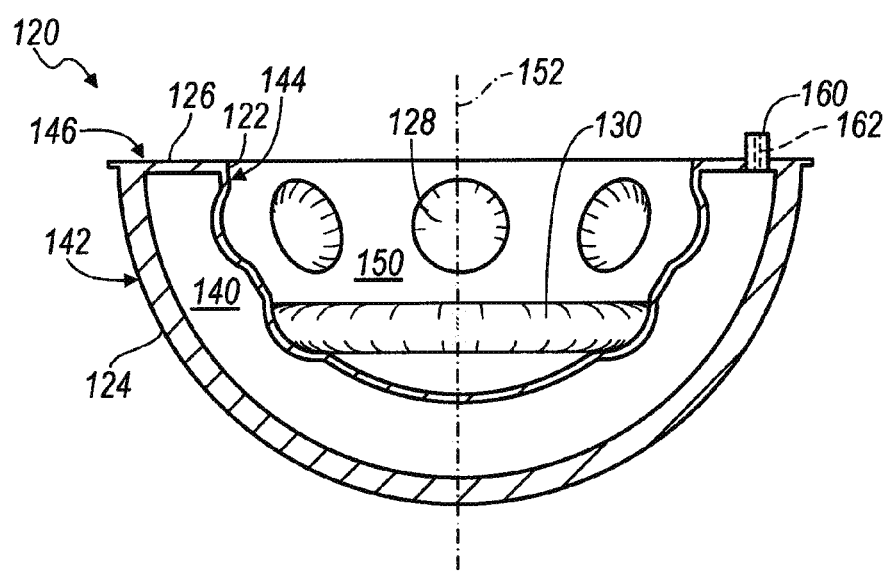
FIG. 3 is a cross-sectional view of a shell, according to various embodiments.

With reference to FIG. 3, an acetabular shell 120 is illustrated. The acetabular shell 120 can include portions similar to those described in the acetabular shell 20 and we have mentioned here only briefly. For example, the acetabular shell 120 can include an inner surface 122, an exterior surface 124, and an upper surface 126. The acetabular shell 120 can further include one or more liner fixation portions. The liner fixation portions can include one or more individual intrusions or negative protrusions 128 and a singular or annular negative protrusion or intrusion 130. The external surface 124 can be a surface of an external wall 142 and the internal surface 122 can be a surface of an internal wall 144. Further, the upper surface 126 can be a surface of an upper wall 146.

The acetabular shell 120 can include an internal or encompassed void 140 similar to the void 40 discussed above. The acetabular shell 120 can further include a fill valve or port 160 having a passage 162 as discussed above. The intrusions 128 and 130 can be formed by the internal wall 144 similar to the positive protrusions as discussed above. According to the embodiment illustrated in FIG. 3, and various embodiments, the intrusions 128, 130 can be formed to extend into or away from an internal liner void 150 of the acetabular shell 120 towards the external wall 142.

The intrusions 128, 130 can move into or towards the liner void 150, such as towards a central axis 152 of the acetabular shell 120, by a pressure provided in the internal or encompassed void 140. As discussed herein, the port 160 can be used to allow filling of the encompassed void 140 to allow the internal wall 144 to deform. Upon deformation of the internal wall 144, the intrusions 128 and 130 can extend or move towards the central axis 152 to positively and fixedly engage a selected feature, such as an acetabular liner, positioned within the acetabular shell 120, as discussed further herein.

Figure 4:
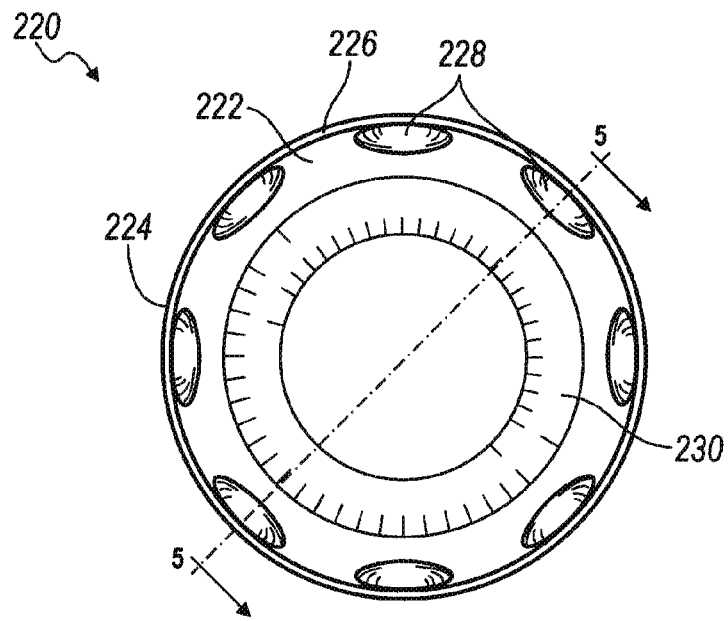
FIG. 4 is a top plan view of a shell, according to various embodiments.
Figure 5:
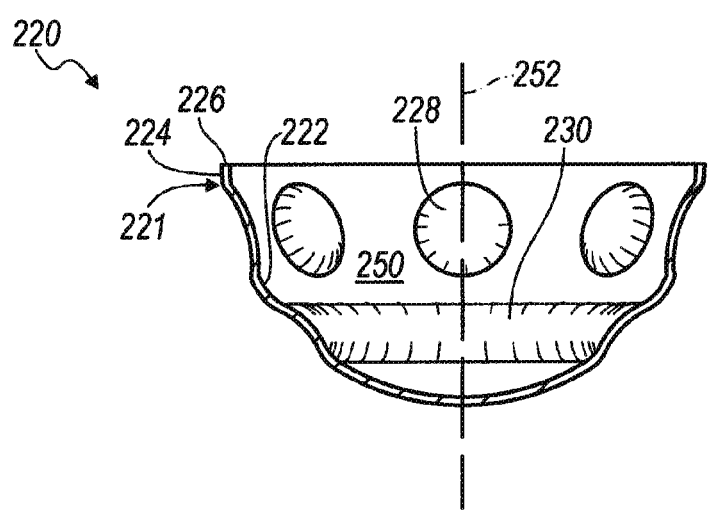
FIG. 5 is a cross-sectional view along lines 5-5 of the acetabular shell of FIG. 4.

Turning reference to FIGS. 4 and 5, an acetabular shell 220 is illustrated. Acetabular shell 220 can include an internal surface 222 and an external surface 224 with an upper or rim surface 226 formed therebetween. With specific reference to FIG. 5, the acetabular shell 220 can include a single wall 221 that includes the external surface 222, the inner surface 224, and the upper surface 226. The single wall 221 can includes all of the surfaces, as illustrated in FIGS. 4 and 5.

The single wall 221 can further include liner engaging features. The liner engaging features can include single or individual protrusion or engaging portions 228 and/or a singular and/or annular protrusion 230. The protrusions can include features that deform the wall 221 into an internal void or area 250, such as towards a central axis 252 of the acetabular shell 220. The engaging features can be similar to the engaging features of 28 or 30 discussed above of the acetabular shell 20, but rather than defining an encompassing void, the acetabular shell 220 includes the single wall 221 that can include the protrusions or engaging portions 228 and 230 for engaging a liner, as discussed further herein.

Figure 6:
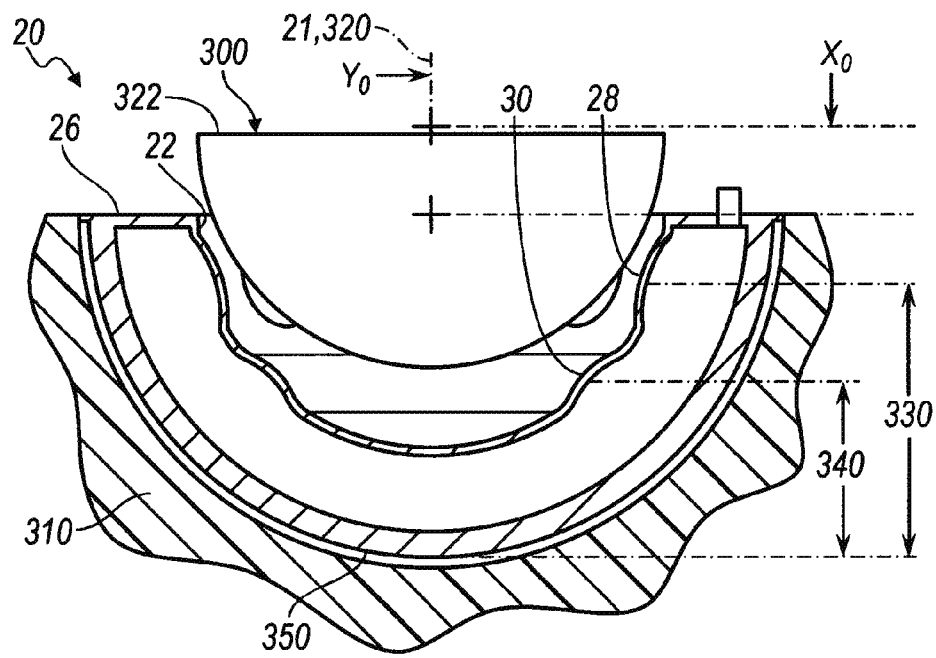
FIG. 6 is a schematic cross-sectional figure of an acetabular shell and a liner in a first position.

Turning reference to FIG. 6, the acetabular shell 20 is illustrated in combination with a selected liner 300. The liner 300 can be any appropriate liner such as a liner formed of ultra-high molecular weight polyethylene, metal, ceramic, or other appropriate liner materials. The shell 20 can be formed of appropriate materials as well, including metallic materials. For example, various cobalt chrome alloys, stainless steel alloys, titanium or titanium alloys, that are appropriate for implantation into a human patient can be used to form the acetabular shell 20, or the acetabular shell according to various embodiments. Generally, the acetabular shell 20 can be formed of a material and/or an appropriate thickness that allow for deformation of the liner engaging features, including the protrusions 28 and 30, to engage the liner 300. As illustrated in FIG. 6, the shell 20 can be positioned relative to an acetabulum 310. The liner 300 can be positioned relative to the implanted shell 20, according to various configurations. The acetabular shell 20 can be implanted into the acetabulum 310 in an appropriate manner, such as engaging the upper shell wall 26 for driving or forcing the shell 20 into the acetabulum 310. The shell 20 can further be fixed into the acetabulum 310 with appropriate features, such as adhesives, a bone in-growth layer, or other appropriate mechanisms.

The shell 20, when positioned within the acetabulum 310, can engage or receive the liner 300. The liner 300 can be positioned at an entry or receiving position relative to the shell 20. For example, the liner 300 can have a central axis 320 that can be positioned relative to a central axis 21 of the shell 20. The liner 300 can have an initial position where the liner axis 320 is offset by zero degrees or zero millimeters (mm) $Y_0$ relative to the central axis 21 of the shell 20. For example, in the initial position, the liner 300 further has an upper rim 322 of the liner 300 that is a first distance $X_0$, such as about 5 mm to about 20 mm, from the top surface 22 of the shell 20. Accordingly, as illustrated in FIG. 6, the liner 300 can be positioned at an initial position where the distance of the top 322 of the liner 300 is a distance $X_0$ relative to the top surface 222 of the shell 20 and the central axis 320 of the liner 300 is offset the distance $Y_0$ from the central axis 21 of the shell 20.

At the $X_0$, $Y_0$ position the liner 300, as illustrated, is not fixedly engaging an initial or first fixation feature, such as the individual protrusion 28 of the shell 20. It is understood, however, that the liner 300 may contact (e.g. touch) without being fixedly engaged to any fixation feature at the $X_0$, $Y_0$ position. As illustrated in FIG. 6, and illustrated above, the protrusion features or fixation features can have a first of distal fixation distance 330, such as defined by the individual protrusions 28, and a second protrusion distance 340, such as defined by the second protrusion or fixation portion 30. The two distances 330 and 340 can be different relative to an apex 350 of the upper surface 26 of the shell 20. Accordingly, the respective distances or the difference between the distances 330 and 340 can be used to selectively position the liner 300 within the shell 20, as discussed further herein.

Figure 7:
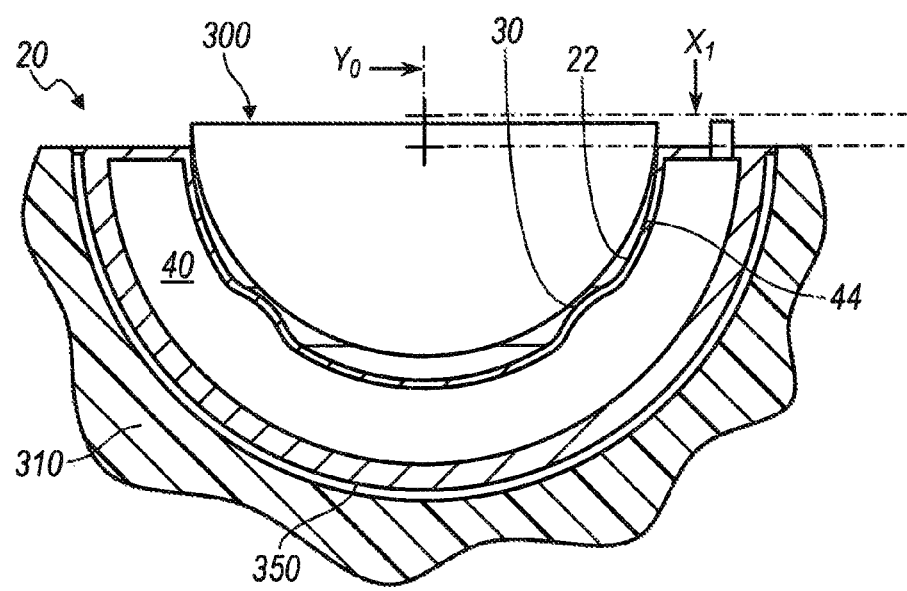
FIG. 7 is a schematic cross-sectional view of a shell and a liner in a second position.

As discussed above in relation to FIG. 6, the liner 300 can be positioned relative to the shell 20 prior to fixation at an initial position $Y_0$, $X_0$. After at least a partial insertion of the liner 300 into the shell 20, a certain number of the engaging protrusions can be depressed or deformed relative to the inner surface 22 of the shell as, illustrated in FIG. 7. The individual protrusions 28 have been deformed to no longer substantially protrude from the inner wall 44. In other words, the protrusions 28 have been substantially deformed to be generally continuous with the surrounding wall portion 44 at the inner surface. In embodiments, the surrounding wall portion 44 may be deformed beyond a neutral state, such as changing from a positive protrusion (e.g. extending into the shell interior) to a negative protrusion (e.g. extending away from the interior of the shell). The annular protrusion 30, as illustrated in FIG. 7, remains extending into the inner area 50 to engage or contact the liner 300. The configuration illustrated in FIG. 7 shows the liner 300 moved a first distance into the shell 20. Where the first distance is $X_0$ minus $X_1$, and where $X_0$ represents the initial position of the liner 300 and $X_1$ represents a first new position of liner 300. The liner 300, however, has not been completely moved into the shell 20.

Due to the inclusion of the protrusion 30 and the deformable protrusions 28, however, the liner 300 can be maintained at the first new position $Y_0$, $X_1$ where the liner 300 can be implanted into a patient for articulation with another portion, such as a femoral head or prosthesis. The shell 20 can have the internal void 40 filled with an appropriate material, such as a non-compressible liquid or material, including the bone cement. The non-compressible material can ensure the wall 44 maintains the configuration after the liner 300 has been moved to the first position. The first new position, therefore, can include the $Y_0$ position as well as the $X_1$ position. Accordingly, the liner 300 can be implanted at least the first position illustrated in FIG. 7.

Figure 8:
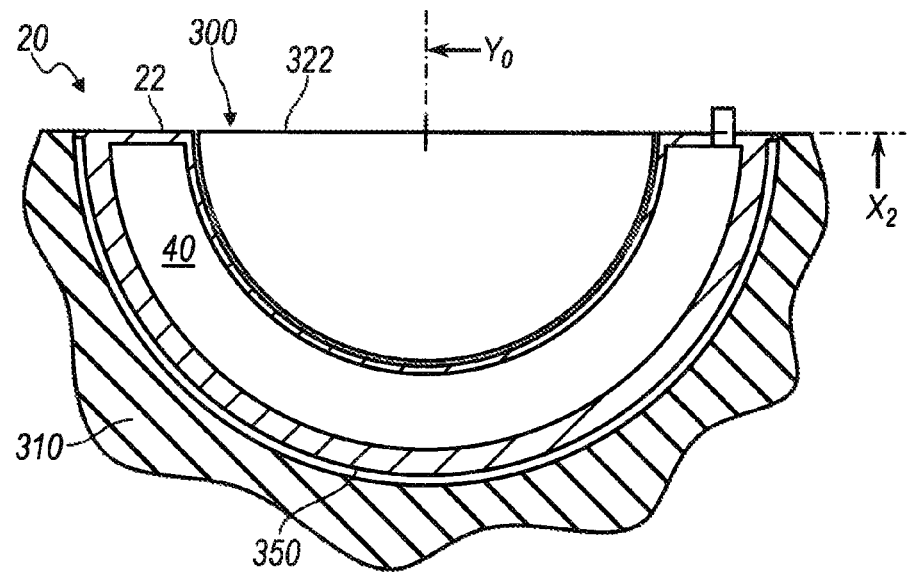
FIG. 8 is a schematic cross-sectional view of a shell and a liner in a third position.

With reference to FIG. 8, the liner 300 can be moved a second distance, at least a second position $X_2$ and the $Y_0$ position. In the second position $X_2$, the liner 300 can be positioned a maximum distance within the shell 20. The second position $X_2$ can include a second distance of movement that is greater than the first distance of movement of the liner 300 into the shell 20.

The liner 300 can, therefore, move or deform both the individual protrusions 28 and the annular protrusion 30. The void 40 can be filled with an appropriate material to fully engage the liner 300 for completing the implantation. Accordingly, the liner 300 can be positioned at least at two positions relative to the shell 20, using the first individual protrusions 28 and the annular protrusion 30. The two positions $X_1$ and $X_2$ are distances of the upper liner wall 322 relative to the upper shell surface 22. Both of the distance positions $X_1$ and $X_2$, however, can include the same $Y_0$ position.

Figure 9:
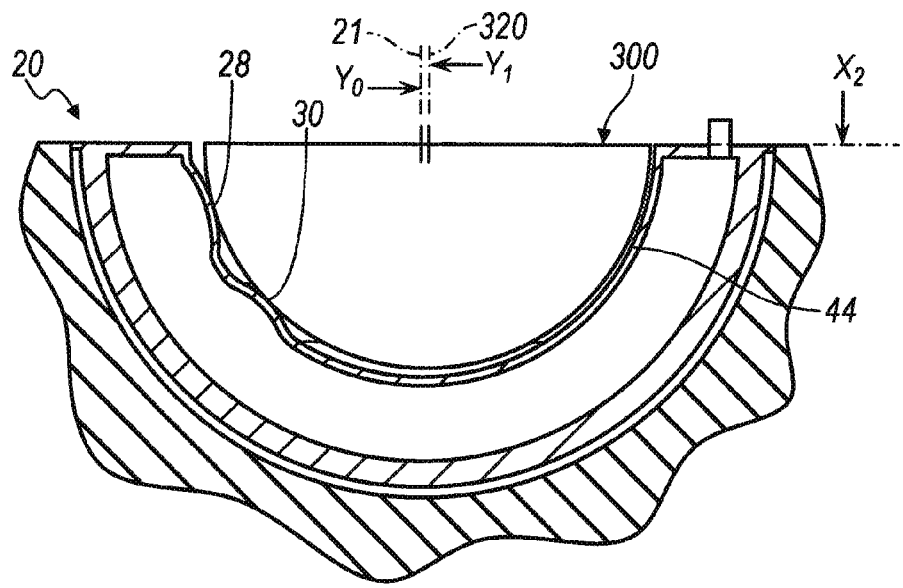
FIG. 9 is a cross-sectional view of a shell and a liner in a third position.

With reference to FIG. 9, the liner 300 can also be offset or moved relative to the central axis 21 of the shell 20. As illustrated in FIG. 9, the liner 300 can be moved to a first new position $Y_1$ to offset the central axis 320 of the liner 300 from the central axis 21 of the shell 20. The distance to $Y_1$ can be the $Y_1$ position minus the $Y_o$ position, where the $Y_o$ position is the initial position and $Y_1$ is the new position. The offset can be by engaging, depressing, and/or deforming the engagement protrusions on one side of the shell 20, while maintaining the protrusions on a second side. Accordingly, as illustrated in FIG. 9, on the right side of FIG. 9, the protrusions have been deformed into the inner wall 44. However, on the left side of FIG. 9, the protrusions 28 and 30 remain substantially undeformed. Accordingly, the shell 20 allows for the liner 300 moved or positioned anteromedially, posterolaterally, superiorly, inferiorly or any position offsetting the central axis 320 from the central axis 21 of the shell 20.

It is understood that any combination of the distance of insertion, as illustrated in FIGS. 7 and 8, and axial offset, as illustrated in FIG. 9, can be achieved. Accordingly, the liner 300 can be moved into the shell to a depth $X_1$ position, as illustrated in FIG. 7, and offset by the distance at $Y_1$ position, as illustrated in FIG. 9. Accordingly, a depth and side offset can be achieved by moving or deforming a selected portion of the protrusions or liner fixation portions of the shell 20. Further, it is understood that the shell 20, or any shell according to various embodiments, can include any selected number and/or size of the liner fixation members. The shell 20, for example, can include 3, 4, or only 1 row of the liner fixation portions. Accordingly, the shell can be moved to a plurality of depths, including 1, 2, 3 or 4 relative to the shell 20. As illustrated in FIGS. 7 and 8, the liner 300 can be moved to two different and distinct depths within the shell 20 using the two rows or positions of liner fixation portions. It is understood that any appropriate number of liner fixation portions, however, can be provided to allow for a greater number of possible positions.

The shell 20, or the shell according to any of the appropriate embodiments, can also include liner engagement portions that also can be partially deformed. Accordingly, a limited number of liner fixation portions can be partially deformed, so as not completely pressed into the wall 44, to allow for a greater range of possible positions of the liner 300 within the shell. The shell can include a plurality of engagement portions, such as a plurality of protrusions positioned or formed over a substantial area of the wall 44 that can be completely or partially deformed to position the liner 300 and a selected position.

The selected position of the liner 300 can be selected by a user during or prior to an implantation. The position can be selected based on selecting a final anatomical position of the positioned liner, such as based on selecting anteromedially, posterolaterally, superiorly, inferiorly or any position offsetting the central axis 320 from the central axis 21 of the shell 20. This selection can, for example, be based on a selected anteversion. For example, the shell 20 can be provided to position a single liner, such as the liner 300, at one of a plurality of depths. The shell 20, therefore, can be implanted into the patient and during a trialing phase, the final desired position or selected position for the liner 300 can be determined and achieved by positioning the liner 300 within the shell 20. The shell 20, therefore, can be provided for a plurality of different positions of the liner 300 without a requiring a plurality of shell sizes and/or thicknesses. The shell 20, or the shell according to various embodiments, including the deformable liner engagement portions, can therefore be used as a single member design for a plurality of individual patients.

Figure 10:
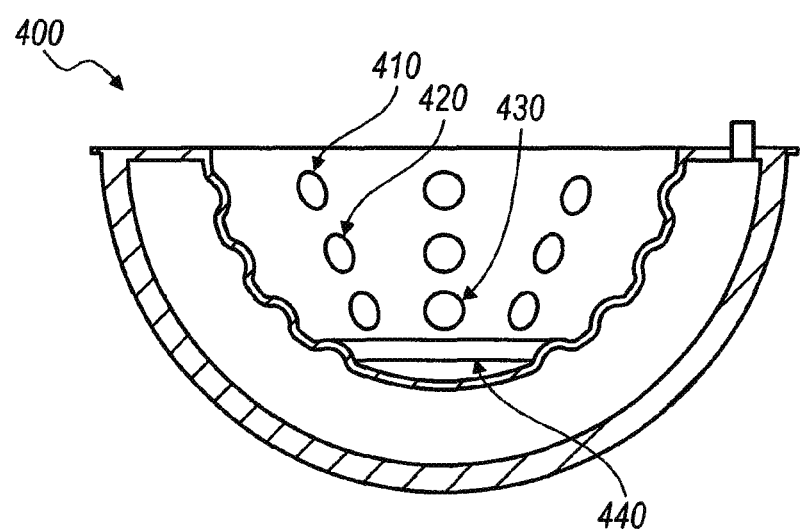
FIG. 10 is a cross-sectional view of an acetabular shell, according to various embodiments.

As noted above, the liner fixation members or portions can be provided in a plurality of rows or positions within a shell. For example, as illustrated in FIG. 10, a shell 400 can have a first row of liner fixation portions 410, a second row of liner fixation portions 420, a third row of liner fixation portions 430, and a fourth row of liner fixation portions 440. The four rows of fixation portions 410-440 can be selectively engaged by the liner 300, in a manner similar to that discussed above, to position the liner 300 at any appropriate position within the shell 400. Accordingly, it is understood that the shell can include more than two regions of liner fixation portions. It is further understood, however, that any appropriate number of liner fixation regions can be provided for providing a selectable position of the liner 300 within the shell based upon a user, such as the surgeon's, selection and/or preference. Accordingly, it is understood that the liner fixation portions may not need to be provided in rows, but may be provided in the shell in any selected configuration to allow for a user to position a liner in a shell as a desired position.

The shell, according to various embodiments, can be formed of appropriate materials of appropriate thicknesses. Generally, the wall of the shell including the liner engaging features is stiff enough between the liner engaging regions to retain a selected or pre-formed shape while the liner engaging portions deform. Therefore, the regions between the liner engaging features may be thicker or formed of stiffer material than the liner engaging regions. For example, the shell 20 may be formed of a stainless steel alloy, such as one that is appropriate for implantation into a human patient. In various embodiments, the protrusions 28, 30 may have a thickness that is about 20% to about 50% less than the remainder of the internal wall 44.

Further, it is understood that liner fixation mechanisms can be used in addition to or in combination with the liner fixation portions, such as the protrusions 28, 30, discussed above. For example, a snap ring or other liner fixation mechanism can be provided. A snap ring can be provided to compress during insertion of the liner 300 and then expand to engage both a depression in the shell and a depression in the liner 300. Snap ring locking mechanism may include those such as the RingLoc® Locking Mechanism sold by Biomet, Inc. It should be noted, however, that additional locking mechanisms may be utilized to secure the liner to the shell, such as cement, deforming polyethylene barb, or any other securement feature known in the art. Thus, the liner can be held within the shell according to various embodiments.

Figure 11:
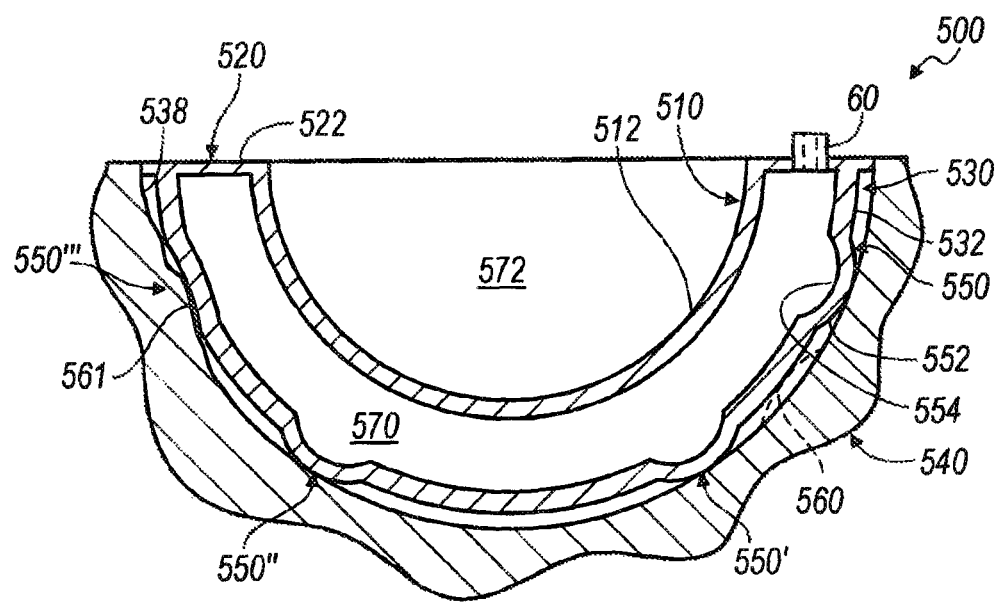
FIG. 11 is a cross-sectional view of an acetabular shell schematically illustrated in an acetabulum, according to various embodiments.

Further, according to various embodiments, as illustrated un FIG. 11, a shell 500, such as an acetabular shell that can be similar to the shells illustrated above, such as the shell 20 illustrated in FIG. 1. The acetabular shell 500 can include an internal wall 510 that has an internal surface 512 that can be provided for articulation with a selected member, such as a femoral head, or for engaging of an acetabular liner. It is understood that the liner can be positioned within the acetabular shell 500 in any appropriate manner including adhesives, a locking member, or other holding or locking feature. The liner positioned within the acetabular shell 500 can be similar to the liner 300 illustrated and discussed above. The internal wall 510 that has the surface 512 can be similar to internal walls as surfaces of generally known acetabular shells such as the acetabular shell in the Regenerex® Ringloc® Modular Acetabular System, sold by Biomet, Inc., having a place of business in Indiana, USA.

The acetabular shell 500 can further include an upper wall 520 that has an upper surface 522 that can extend to an exterior wall 530. The exterior wall 530 can have an exterior surface 532 that can generally define or form an exterior contacting surface, such as the contact and acetabulum 538 of a pelvis 540. The acetabulum 538 can have a selected size that can be provided with an acetabular prosthesis, such as the acetabular shell 500 that can fit within the acetabulum 538. It is understood that the acetabulum can be prepared with a selected instrument to receive the prosthesis 500.

The external wall 532 can include one or more protrusions 550 that can have an external or bone contacting surface 552 and an internal surface 554. The bone contacting surface 552 of the one or more protrusions 550 can contact the acetabulum 538 and be deformed by a force applied to the acetabular shell 500, such as with an implantation tool (not illustrated). The protrusion 550 can contact and deform upon the application of a force between the acetabular shell 500 and the acetabulum 538. The bone contacting protrusion 550 can deform in an appropriate manner or amount until the acetabular shell 500 is at a selected position relative to the acetabulum 538. As illustrated in FIG. 11the bone contacting protrusions can include at least a first contacting protrusion 550, a second bone contacting protrusion 550', a third bone contacting protrusion 550'', and a third and fourth bone contacting protrusion 550'''. Each of the bone contacting protrusions 550-550''' can contact the acetabulum and deform an appropriate amount for positioning the acetabular shell 500 within the acetabulum 538.

The acetabular shell 500, at least in part due to the bone contacting protrusions 550-550''', can be used and/or positioned in at least one of a selected plurality of acetabulums. Each of the possible implantable acetabulums may have different characteristics, such as shape, size, configurations, and the protrusions 550 allow for use of the single shell 500 in each. For example, the protrusions 550-550''', or any appropriate number or configuration of the protrusions, can deform to allow the single acetabular shell 500 to be positioned in an acetabulum selected from a range of sizes (i.e. internal diameter). Accordingly, the external geometry of the acetabular shell 500 can be augmented by the deformation of the protrusions 550-550''' to allow for the single acetabular shell 500 to be positioned in a selected acetabulum.

Further, specific or unique defects or shapes of the acetabulum 538 can be accommodated with the bone contacting protrusions. For example, a bone projection or bone growth 560 or 560a can be positioned to between a plurality of the protrusions 550, 550' or to contact to deform one or more of the bone contacting protrusions 550'''. Further, the protrusions, or one or more of the bone contacting protrusions 550-550''' can deform to reduce the external dimensions of the acetabular shell 500 to fit into a selected size acetabulum The bone contacting protrusions 550-550''' can include features, geometries, and other specifics, such as thicknesses and positioning, similar to the protrusions discussed above, such as the protrusion 28 in the acetabular shell 20. The bone contacting protrusions 550-550''', however, can be formed in or by the exterior wall 530 to contact the bone of the acetabulum 538. The force applied to the acetabular shell 500 may then deform the exterior bone contacting protrusions 550-550''' to allow for a selected positioning, size, and accommodation of an acetabular geometry. The single acetabular shell 500, therefore, can fit into a plurality of sizes of acetabulums without requiring multiple manufacturing and/or storing a plurality of sizes of acetabular shells. Also, the acetabular shell 500 can be intraoperatively positioned at an optimal or user-selected position by selectively and appropriately deforming one or more of the bone contacting protrusions 550-550'''. Accordingly, the acetabular shell 500 may have an offset, angle, depth, or other position selected during an operative procedure. For example, once the acetabulum is prepared and the shell 500 is initially or partially inserted, a user can selectively deform one or more of the protrusions 550-550''' to achieve a selected position of the shell 500 within the acetabulum. The selected position can be selected after the initial positioning of the shell 500.

With continued reference to FIG. 11, the acetabular shell 500 can include features similar to that of the acetabular shell discussed above, such as the acetabular shell 20 illustrated in FIGS. 1 and 2. For example, a valve or port 60 can be provided to allow access to an internal void 570 that is defined by the internal wall 510, top wall 520, and exterior wall 530. The void 570 can be filled with a non-compressible material to position or fix the acetabular shell 500 in a selected position and to fix a selected deformation of the bone contacting protrusions 550-550'''. Moreover, the internal wall 510 that has a surface 512 can define a liner receiving void 572 into which a liner can be positioned or fixed. It is understood, however, that the acetabular shell 500 can also be formed for articulation directly with a femoral prosthesis and/or a natural femoral head. The bone contacting protrusions 550 can extend away from the void 570 such that a negative area is defined within the void 570 relative to each of the bone contacting protrusions 550-550'''. The bone contacting protrusions 550-550''', for example the protrusion 550''', can be deformed into the individual protrusion voids or negative areas defined by each of the protrusions and/or into the void 570 divided by the acetabular shell 500.

Figure 12:
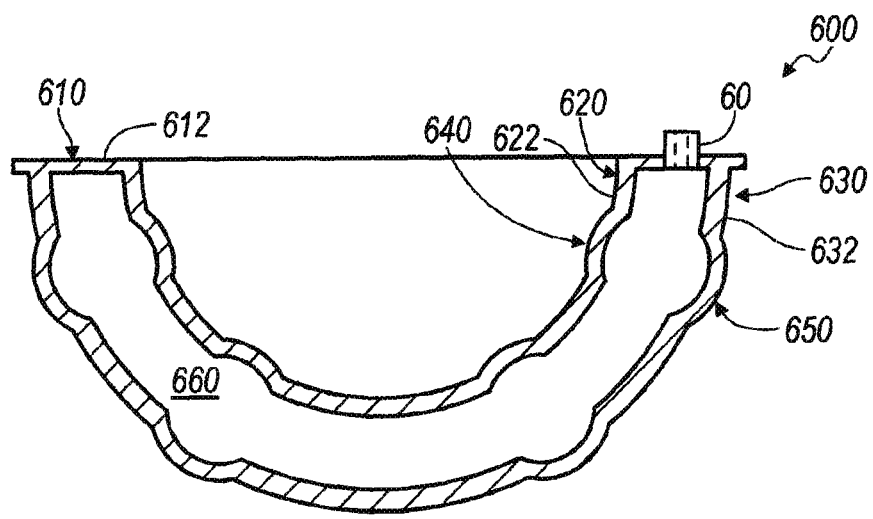
FIG. 12 is a cross-sectional view of an acetabular shell, according to various embodiments.

With reference to FIG. 12, an acetabular shell 600 is illustrated. The acetabular shell 600 can include a top wall 610 that has a top surface 612. The acetabular shell can further include an internal wall 620 that has an internal surface 622 and an external wall 630 that can have an external surface 632. The internal wall 620 can have formed therein a first set of internal protrusions 640 that can be similar to the protrusions illustrated above, such as the protrusion 28 of the acetabular shell 20 illustrated in FIG. 2. The internal protrusion may, for example, contact a liner, such as the liner 300. Further, the exterior wall 630 can include exterior or bone contacting protrusions 650 that can be similar to the bone contacting protrusions 550-550''' illustrated in FIG. 11. It is understood, therefore, that a single acetabular shell, such as the acetabular shell 600 can include both the bone contacting protrusion 650 and the internal protrusion 640. The single acetabular shell 600, therefore, can provide selectable deformation of the exterior wall 630 and the interior wall 620 for positioning the acetabular shell 600, itself, within an acetabulum, such as the acetabulum 538, and for selectively positioning a liner relative to the acetabular shell 600.

Thus the single acetabular shell 600 can be provided to allow for variability of both positioning of the acetabular shell 600 within the acetabulum and variability of positioning a liner within the acetabular shell 600. It is understood that the bone contacting protrusions 650 and the liner contacting or inner protrusions 640 can include features and specifications similar to those discussed above, such as size, shape, thickness, geometry, and other features. Nevertheless, one skilled in the art will understand that the single acetabular shell 600 can include both external and internal protrusions.

The acetabular shell 600 can further include or define an internal void 660 where each of the protrusions 640 and 650 can also define or form negative regions relative to the internal void 660 for each of the respective protrusions to deform into. The protrusions 640 and 650 may also deform into a void 660, such as described above. Also, the shell can include the port 60 for filling the void 660 with a non-compressible material, as discussed above.

It is understood that the various features discussed hereinabove can be included in multiple configurations and the specific embodiments illustrated in the various drawings are not mutually exclusive from one another, unless otherwise specified. Accordingly, as illustrated in FIG. 12, the acetabular shell 600 can include protrusions both on an internal wall surface and an external wall surface that can deform relative to other portions, such as a liner and/or an acetabulum. The protrusions and/or negative areas, as discussed above, can deform for positioning the acetabular shell, according to various embodiments, within an acetabulum. Also, protrusions can deform to allow for positioning of a liner at a selected and selectable position within the respective shells. Accordingly, one skilled in the art will understand that the acetabular shells, according to various embodiments can be designed and formed for selectable, such as user selectable, positioning of the shell relative to an acetabulum and a liner relative to the shell.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Further, it is understood that various features illustrated in one example embodiments may be employed together or to replace features in other example embodiments.

What is claimed is:

1. A prosthesis system for placement in a subject, comprising:
   an acetabular shell having a first wall including an acetabular liner receiving cavity and an upper rim surface, the acetabular shell further defining a central axis and an apex spaced apart from the upper rim surface relative to the central axis; and
   an acetabular liner, wherein the acetabular shell is configured to at least partially receive the member acetabular liner in the acetabular liner receiving cavity; and
   wherein the first wall of the acetabular shell includes an acetabular liner fixation portion;

wherein the acetabular liner fixation portion is configured to deform to contact the acetabular liner and engage the acetabular liner at a selected position relative to the acetabular shell, and wherein the acetabular liner fixation portion of the first wall of the acetabular shell is one of a plurality of acetabular liner fixation portions spaced apart relative to the acetabular shell and spaced apart relative to one another circumferentially along the first wall;

wherein the acetabular shell has a second wall spaced apart from the first wall; and wherein the second wall and the first wall at least in part define an enclosed void defined by the acetabular shell.

2. The prosthesis system of claim 1, wherein the acetabular liner fixation portion includes a portion of the first wall that has a negative protrusion portion that extends away from an acetabular liner receiving void of the acetabular shell.

3. The prosthesis system of claim 1, wherein a first sub-plurality of acetabular liner fixation portions are positioned nearer the upper rim surface of the acetabular shell than a second sub-plurality of acetabular liner fixation portions;

wherein the acetabular liner is configured to deform substantially only the first sub-plurality of acetabular liner fixation portions to be positioned at a first position relative to the acetabular shell and deform both the first sub-plurality of acetabular liner fixation portions and the second sub-plurality of acetabular liner fixation portions to be positioned at a second position relative to the acetabular shell;

wherein the second position is nearer the apex of the acetabular shell that is spaced apart from the upper rim surface of the acetabular shell.

4. The prosthesis system of claim 1, wherein the acetabular liner fixation portion is configured to selectively engage the acetabular liner in at least one of a substantially non-deformed configuration to position the acetabular liner at a first position relative to the upper rim surface or in a deformed configuration to position the acetabular liner at a second position relative to the upper rim surface.

5. The prosthesis of claim 1,
wherein each acetabular liner fixation portion of the plurality of acetabular liner fixation portions includes a deformable region configured to change shape relative to a surrounding region of the first wall.

6. A prosthesis system for placement in a subject, comprising:
a first member having a first wall;
a second member, wherein the first member is configured to at least partially receive the second member; and
wherein the first wall of the first member includes a second member fixation portion;
wherein the second member fixation portion is configured to deform to contact the second member and engage the second member at a selected position relative to the first member,
wherein the second member fixation portion of the first wall of the first member is one of a plurality of second member fixation portions spaced apart relative to the first member and spaced apart relative to one another circumferentially along the first wall, and
wherein the second member fixation portion includes a portion of the first wall that has a negative protrusion portion that extends away from a second member receiving void of the first member.

7. A prosthesis system for placement in a subject, comprising:
a first member having a first wall;
a second member, wherein the first member is configured to at least partially receive the second member; and
wherein the first wall of the first member includes a second member fixation portion;
wherein the second member fixation portion is configured to deform to contact the second member and engage the second member at a selected position relative to the first member,
wherein the second member fixation portion of the first wall of the first member is one of a plurality of second member fixation portions spaced apart relative to the first member and spaced apart relative to one another circumferentially along the first wall,
wherein a first sub-plurality of second member fixation portions are positioned nearer an upper rim of the first member than a second sub-plurality of second member fixation portions;
wherein the second member is configured to deform substantially only the first sub-plurality of second member fixation portions to be positioned at a first position relative to the first member and deform both the first sub-plurality of second member fixation portions and the second sub-plurality of second member fixation portions to be positioned at a second position relative to the first member, and
wherein the second position is nearer an apex of the first member that is spaced apart from the upper rim of the first member.

* * * * *